US007736391B2

(12) United States Patent
Schwibner et al.

(10) Patent No.: US 7,736,391 B2
(45) Date of Patent: Jun. 15, 2010

(54) COSMETIC AND RECONSTRUCTIVE PROSTHESES WITH A MICROENCAPSULATED BIOLOGICALLY COMPATIBLE RUPTURE INDICATOR FOR SUSTAINED RELEASE AND METHODS OF DETECTING COMPROMISE OF A PROSTHESIS

(75) Inventors: Barry H. Schwibner, Boca Raton, FL (US); Thomas C. Roballey, Huntington, CT (US); Nathan Feldman, Deerfield Beach, FL (US)

(73) Assignee: TONABA HealthScience II, LLC, Deerfield Beach, FL (US)

( * ) Notice: Subject to any disclaimer, the term of this patent is extended or adjusted under 35 U.S.C. 154(b) by 1125 days.

(21) Appl. No.: 11/378,983

(22) Filed: Mar. 17, 2006

(65) Prior Publication Data
US 2006/0161266 A1 Jul. 20, 2006

Related U.S. Application Data

(63) Continuation-in-part of application No. 10/918,110, filed on Aug. 13, 2004, which is a continuation-in-part of application No. 10/773,604, filed on Feb. 5, 2004, now abandoned.

(60) Provisional application No. 60/511,707, filed on Oct. 17, 2003, provisional application No. 60/445,227, filed on Feb. 6, 2003, provisional application No. 60/662,906, filed on Mar. 17, 2005.

(51) Int. Cl.
*A61F 2/12* (2006.01)
(52) U.S. Cl. .......................................................... 623/8
(58) Field of Classification Search ................ 623/7, 623/8
See application file for complete search history.

(56) References Cited

U.S. PATENT DOCUMENTS

| 3,954,102 | A | 5/1976 | Buuck ........................ 128/79 |
|---|---|---|---|
| 4,100,627 | A | 7/1978 | Brill, III ........................ 3/36 |
| 4,455,691 | A | 6/1984 | Van Aken Redinger et al. .. 3/36 |
| 4,472,226 | A | 9/1984 | Redinger et al. ............ 156/242 |
| 4,795,463 | A | 1/1989 | Gerow ........................... 623/8 |
| 4,897,268 | A | 1/1990 | Tice et al. ................... 424/422 |
| 4,969,899 | A | 11/1990 | Cox ............................... 623/8 |
| 5,288,504 | A | 2/1994 | Versic ........................ 424/497 |
| 5,630,844 | A | 5/1997 | Dogan et al. ................... 623/8 |
| 5,817,343 | A | 10/1998 | Burke ........................ 424/489 |
| 5,912,015 | A | 6/1999 | Bernstein et al. ............ 424/484 |
| 5,989,463 | A | 11/1999 | Tracy et al. ................. 264/4.1 |
| 6,146,418 | A | 11/2000 | Berman ........................ 623/8 |
| 6,183,514 | B1 | 2/2001 | Becker ........................ 623/8 |
| 6,194,006 | B1 | 2/2001 | Lyons et al. ................ 424/489 |
| 6,290,983 | B1 | 9/2001 | Rickey et al. .............. 424/426 |
| 6,296,842 | B1 | 10/2001 | Jaworowicz et al. ..... 424/78.02 |
| 6,361,798 | B1 | 3/2002 | Thanoo et al. ............. 424/489 |

(Continued)

*Primary Examiner*—Thomas J Sweet
(74) *Attorney, Agent, or Firm*—St. Onge Steward Johnston & Reens LLC

(57) ABSTRACT

A prosthesis for implant in a human patient body has an external envelope, at least one implant filling material, and at least one biologically compatible rupture indicator encapsulated in a sustained release delivery vehicle and disposed in a carrier medium, the rupture indicator capable of leaking out of upon rupture of the external envelope and triggering a signal detectable by the patient as it is released from the delivery vehicle, allowing for detection of a rupture or impending rupture by the patient.

15 Claims, 3 Drawing Sheets

U.S. PATENT DOCUMENTS

| | | | |
|---|---|---|---|
| 6,379,703 B1 | 4/2002 | Lyons et al. | 424/489 |
| 6,455,074 B1 | 9/2002 | Tracy et al. | 424/501 |
| 6,479,065 B2 | 11/2002 | Jaworowicz et al. | 424/423 |
| 6,596,316 B2 | 7/2003 | Lyons et al. | 424/489 |
| 6,793,938 B2 | 9/2004 | Sankaram | 424/489 |
| 2002/0055757 A1 | 5/2002 | Torre et al. | 606/192 |
| 2003/0180352 A1 | 9/2003 | Patel et al. | 424/465 |
| 2005/0033132 A1 | 2/2005 | Shults et al. | 600/347 |

COSMETIC AND RECONSTRUCTIVE PROSTHESES WITH A MICROENCAPSULATED BIOLOGICALLY COMPATIBLE RUPTURE INDICATOR FOR SUSTAINED RELEASE AND METHODS OF DETECTING COMPROMISE OF A PROSTHESIS

CROSS-REFERENCE TO RELATED APPLICATIONS

This application is a continuation-in-part of U.S. patent application Ser. No. 10/918,110 filed Aug. 13, 2004, which in turn is a continuation-in part of U.S. patent application Ser. No. 10/773,604, filed on Feb. 5, 2004 now abandoned. Application Ser. No. 10/918,110 claims the benefit under 35 U.S.C. §119(e) of the U.S. Provisional Patent Application Ser. No. 60/511,707, filed on Oct. 17, 2003, and application Ser. No. 10/773,604 claims the benefit under 35 U.S.C. §119 (e) of U.S. Provisional Patent Application Ser. No. 60/445,227, filed on Feb. 6, 2003. The present application also claims the benefit under 35 U.S.C. §119 (e) of the U.S. Provisional Patent Application Ser. No. 60/662,906 filed on Mar. 17, 2005. All prior applications are herein incorporated by reference in their entirety.

FIELD OF THE INVENTION

The present invention relates to a cosmetic and reconstructive prosthesis having a biologically compatible rupture indicator and methods of detecting compromise or rupture of the prosthesis. More particularly, the present invention relates to a prosthesis comprising a biologically compatible rupture indicator contained within microcapsules or microparticles having a sustained release profile.

BACKGROUND OF THE INVENTION

Cosmetic and reconstructive implants are widely used in cosmetic and reconstructive corrections. One of the commonly use substances as the implant filling material is silicone gel. It has been used for various facial implants, such as brow, nose, cheek, chin and lips, and various body implants, such as pectoral and breast, triceps and biceps, genitals, buttocks and calf. Among all types of cosmetic and reconstructive implants, the breast implant is the most prevalent and, hence is addressed with specific emphasis hereinafter.

Over the last four decades, surgical breast augmentation in the United States has been primarily achieved through placement of breast implants. Implants are surgically placed either in front of the pectoralis major muscle, called subglandular or prepectoral implants, or they are placed behind the pectoralis major muscle, called submuscular, retroglandular, retropectoral, or subpectrol implants. The type of the material in the implants and the variations in the shape and supporting shells of the implant may also vary. A silicone gel-filled implant is generally composed of silicone gel contained within a silicone polymer membrane or envelope. A saline implant is generally composed of saline contained within a silicone polymer membrane. A double-lumen implant generally refers to an implant having two shells, typically an inner shell filled with silicone gel surrounded by an outer shell filled with saline. A reverse double-lumen implant generally refers to an inner shell of saline surrounded by silicone. Other variations have been implanted with three or more shells.

Before 1992, the majority of breast augmentation implants in the United States contained silicone gel. This was due to general acceptance by the medical community at the time, surgeons' preference, and the reported better texture and "feel" of a silicone gel-filled implant versus a saline-filled implant by the patients. It has been estimated that over one million women in the United States alone have received silicone gel-filled breast implants. In the 1980s, independent authors questioned a possible association between silicone gel-filled implants and the subsequent development of connective-tissue diseases. Fueled by media hype and class action lawsuits, the Food and Drug Administration (FDA) was asked to analyze the data and make a decision. In 1992, the FDA announced that breast implants containing silicone gel would only be available in the United States under clinically controlled trials. It has since been primarily restricted in the United States to women undergoing post-mastectomy reconstruction and those requiring secondary surgery after breast augmentation. Saline-filled breast implants have replaced silicone gel-filled implants as the common breast prosthesis in the past decade. However, in comparison to silicone gel-filled implants, saline-filled breast implants are inferior in terms of mimicking elasticity, feel, and movement of the natural breast tissue. Since 1992, there are many studies investigating the safety concerns of the silicone gel-filled implants. In 1999, after reviewing dozens of studies, the Institute of Medicine (IOM) concluded in its landmark 1999 report that silicone gel-filled implants do not cause the autoimmune disorders such as lupus or arthritis. The main safety concern according to the report is the implants' tendency to rupture. The silicone can bleed or leak out of its shell, causing infections, and/or local tissue reactions. The IOM 1999 report became the turning point for the breast implant industry and the plastic surgery profession, opening the door for the return of silicone gel-filled breast implants for cosmetic use.

Silicone gel-filled implant rupture is often locally symptomatic, and continues to be a genuine clinical concern for patients and physicians. In the United States, an estimated one to two million patients, or approximately 1% of the adult female population, have breast implants. Generally, the risk of implant rupture increases with the age of the implant. One recent study revealed that the median lifespan of a silicone gel-filled breast implant is 16.4 years. In that study, 79.1% of implants were intact at 10 years; the percentage decreased to 48.7% at 15 years. Another study revealed that at least 77% of 344 women from Birmingham, Ala. who were not referred for examination had at least one implant that had "ruptured" or had an "indeterminate" finding upon MRI. The reported median implant age at rupture was 10.8 years, and submuscular implants were more likely than subglandular implants to rupture.

In essentially all patients, a fibrous capsule forms around the implant i.e., encapsulation. The capsule may be soft and nonpalpable or hard and resistant. Generally after implantation, two types of silicone gel-filled breast implant ruptures can occur: intracapsular rupture occurs when silicone escapes the elastic membrane shell but is contained in the fibrous capsule. This form of silicone gel-filled breast implant rupture is most common. Extracapsular rupture involves the escape of free silicone gel through the fibrous capsule, with extravasation into the breast tissue. Migration of silicone gel to the axillary lymph nodes also may be present. Furthermore, silicone gel can migrate to the brachial plexus, chest wall, axilla and the wrist.

In attempts of reducing the likelihood of implant rupture, improvements have been made to the structure of the implant envelope or shell. U.S. Pat. Nos. 4,455,691 and 4,472,226 disclose a three layer implant wall comprising a middle layer made of a heteropolymer of dimethylpolysiloxane and siloxane elastomer, which substantially impedes the migration of silicone gel. Commercially, breast implants constructed with low diffusion silicone elastomer shells are available from the INAMED Corporation, Santa Barbara, Calif. The low diffusion shell has a barrier coat between two layers of silicone elastomer to minimize silicone diffusion. U.S. Pat. No. 5,630,844 discloses another three layer implant shell which comprises a hydrophobic thermoplastic elastomer middle layer as a water vapor barrier, which can be used with a broader scope of filling materials and can reduce ruptures due to fold flaw fracture caused by loss of water vapor from the shell.

Furthermore, a new cohesive silicone gel has been developed and is already in use for breast implants in Canada, Europe and other countries. The cohesive silicone gel is expected to be approved for breast implants in the United States in the near future. Different from the silicone gel traditionally used for breast implants, cohesive silicone gel does not leak out from the shell of the implant. However, when the implant shell ruptures, the patient's tissue will be in contact with the cohesive silicone gel, which can potentially cause inflammation and other mal-effects of silicone to the human body.

The diagnosis of silicone gel-filled breast implant rupture is critically useful to both clinicians and patients. It aids in surgical decision-making and helps the patient gain peace of mind. Furthermore, it avoids the risk of any illness to patient, including any potential systemic effects of leaked silicone gel-filled breast implants, if any, which presently remain unclear. Currently, magnetic resonance imaging (MRI) is used to evaluate silicone gel-filled breast implants, because the findings at clinical examination often are nonspecific. However, MRI is an expensive examination involving complex instrumentation and data processing. Having regular-scheduled MRI's to detect a rupture, preferably sooner than later, is impracticable due to the expense, the complicated nature of the procedure, requirement of multiple parties including medical personnel, and inconvenience to patient.

As of this writing, the current state of the art as recommended by the FDA (Food and Drug Administration) for women with gel-filled implants is, that should a women and/or her physician suspect a rupture of an implant, the patient is to be referred for immediate Magnetic Resonance Imaging (MRI) utilizing a breast coil to either rule out or confirm a compromise of the implant. However, what is troubling about this is, when gel-filled implants rupture, they rarely cause pain or other immediate symptoms, therefore the women doesn't know to seek medical care. It has also been recommended that MRI'S, which are extremely costly, be performed every two years as a screening technique. What of the period of time between screening MRI's when even the smallest rupture of the envelope can result in the silicone gel being in contact for a prolonged period with the patient's tissues?

Thus, there remains a need for improved detection methods available to the patient herself to detect a possible rupture or impending rupture, and be warned or signaled that she needs to seek medical attention. Further, there remains a need for improved implants that prevent leakage of implant filling material and also incorporate technology and warning mechanisms such that the implant warns or signals a patient of rupture or impending rupture and leakage, preferably prior to leakage of implant filling material.

SUMMARY OF THE INVENTION

In one aspect of the present invention, a prosthesis for implant in a human patient body comprising an external envelope, at least one implant filling material contained within the external envelope, and at least one biologically compatible rupture indicator encapsulated in a sustained release delivery vehicle and disposed in a carrier medium for placement in the external envelope, the rupture indicator capable of leaking out of upon rupture of the external envelope and triggering a signal detectable by the patient as it is released from the delivery vehicle, is provided.

In another aspect of the present invention, a prosthesis for implant in a human patient body, comprising an external envelope made of at least one layer of a first elastomer; an indicator lumen; a carrier medium disposed within the indicator lumen; and at least one biologically compatible microencapsulated rupture indicator contained in the carrier medium, the rupture indicator capable of leaking out of the indicator lumen upon rupture of the external envelope and triggering a signal detectable by the patient, at least one implant lumen enclosed by at least one implant lumen envelope, the implant lumen disposed within the indicator lumen, and an implant filling material contained within the implant lumen, is provided.

DETAILED DESCRIPTION OF THE INVENTION

Figure 2:
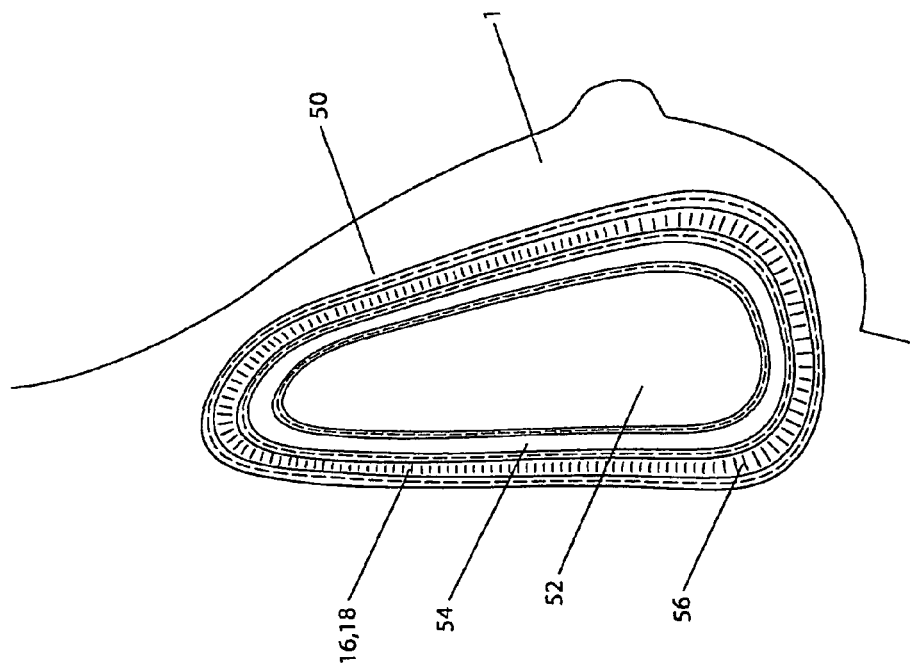
FIG. 2 is a side view of a triple lumen breast prosthesis in a further embodiment of the present invention, which has an internal implant lumen disposed within an external implant lumen and an indicator lumen disposed at the most is exterior of the prosthesis.

Cosmetic and reconstructive prostheses comprising a biologically compatible rupture indicator and methods of detecting compromise or rupture of the prosthesis, are advantageous in warning a patient of a compromise or rupture, preferably prior to the release of the silicone-gel or alternative filling material from the prosthesis. A more detailed description of the prosthesis containing a biologically compatible rupture indicator and methods of detecting compromise or rupture can be found in U.S. patent application Ser. No. 10/773,604 (filed Feb. 5, 2004 and claiming priority to U.S. Provisional Application No. 60/445,227 filed Feb. 6, 2003) and its continuation-in-part U.S. patent application Ser. No.

10/918,110 filed Aug. 18, 2004, with all of these applications incorporated herein by reference.

The implant described by U.S. patent application Ser. Nos. 10/918,110 and 10/773,604 incorporates a rupture indicator that is biologically compatible with the human body, meaning that it is safe and appropriate for placement within the human body. When the prosthesis ruptures, even a minor rupture, chemical indicator leaks out from the implant to contact the surrounding tissues of the patient where it is absorbed into the vascular system of the body. Once the rupture indicator has contacted the patient's tissues and/or entered the patient's system, a signal or warning is triggered. For instance, the rupture indictor, such as phenazopyridine, or a metabolized product thereof, once absorbed into the vascular system of the body, is then transported to the kidneys where it is metabolized and released within the urine. This results in a change to the urine, namely a change in color, that upon urination, the patient could see. For instance, excreted phenazopyridine changes urine color to reddish-orange. This color change to urine, induced by the rupture indicator, is the signal or warning to the patient of rupture or impending rupture of implant filling material and requiring the patient to seek medical attention.

While the implant having this signal or warning to allow self-detection by the patient, as previously disclosed in U.S. patent application Ser. Nos. 10/918,110 and 10/773,604, is an important advancement, the rupture indicators disclosed therein may serve as a signal for a relatively short period of time. For instance, when the biologically compatible rupture indicator phenazopyridine is selected as the rupture indicator, a maximum safe dosage may be placed within the prosthesis, or specifically within the indicator lumen of the prosthesis. Once a rupture and subsequent leakage occurs and the rupture indicator is absorbed and metabolized, this guarantees the maximum period of time during which a patient would have the opportunity to notice the signal or warning released upon compromise or rupture of the prosthesis. This maximum time period may be very limited, for instance, a day or two at most. (For instance, phenazopyridine systemically excretes in 24 hours.) Therefore, a patient must notice within this time period the signal or warning which was caused by the leaking out of the biologically compatible rupture indicator from the compromised or ruptured prosthesis. The signal or warning, in the case of phenazopyride, being a urine color change for visual detection by the patient, may be difficult for certain patients to notice within the short, one to two day, time period. Thus, a short time period for the signal achieved by the rupture indicator may render the prosthesis, in this limited sense, problematic in its ultimate ability to warn the patient of a compromise or rupture.

The shelf life (in vivo and in vitro) of a rupture indicator, such as phenazopyridine, would be very limited without modification of the compound to extend that period. In terms of the in vitro shelf life, this must be divided into two separate time periods. First the actual maximum shelf storage period (packaged) of the prostheses and then the "shelf life" of the rupture indicator within the prostheses after they have been implanted into the body, but prior to release or leakage. With reference to the former, the maximum shelf storage period (packaged) has been determined to be 5 years and the projected life of a breast prosthesis following implantation has been determined to be 10.8 years. Thus, ideally, the indicator should have an in vitro shelf life of 5 years plus 10.8 years for a total of 15.8 years.

Current literature, referencing phenazopyridine specifically cautions against storing the medication in warm, moist places. This, of course, refers to phenazopyridine in its present tablet form. In terms of the effect of temperature on the stability of phenazopyridine, or an alternative biologically compatible rupture indicator in the present invention, the average normal body temperature is 98.6° F. (37° C.). With illness, the body temperature can rise to 106° F. (41° C.) plus, hence, the rupture indicator must be capable of sustaining temperatures in this range.

In terms of the effect of moisture on the stability of phenazopyridine, or an alternative biologically compatible rupture indicator in the present invention, the concept requires the medication to be in solution with a total shelf-life of at least 15.8 years.

The present invention seeks to prolong the length of the signal or warning to the patient, and thus, incorporates rupture indicators having extended or delayed release properties, and/or improved stability under particular temperature and moisture conditions, as described below.

The prosthesis and method according to the present invention provides an extended signal or warning to the patient, when the biologically compatible rupture indicator leaks out from the compromised or ruptured prosthesis and is absorbed into the vascular system of the patient, or a metabolized product thereof, triggering a signal or warning detectable by sight, smell or sensation experienced directly by the patient, allowing a greater time span in which the patient can detect the signal or warning. An extended release of the signal or warning and stabilization of the biologically compatible rupture indicator is achieved.

In one aspect of the present invention, the biologically compatible rupture indicator is encapsulated within microparticles (polymeric particles in the micrometer size range), microspheres, microbeads, microcapsules, nanoparticles (polymeric particles in the nanometer size range), or nanospheres (hereinafter collectively referred to as "microparticles"). The term microparticle refers to any biodegradable polymeric particle having a core substance with the ability to encapsulate agents, specifically a biologically active agent. This results in a microencapsulated agent within microparticles as its carrier, conferring to the agent the qualities of enhanced delivery across a number of natural and artificial membranes, improved bioavailability, and/or sustained release from microparticles, and hence, sustained delivery to (and uptake by) the cells of the body.

Microparticles can be constructed all with specific sphere size and polymer shell thickness, and can be made to release their core substance only after the polymer shell has dissolved (for example, by hydrolysis of the polymeric matrix) to the point of rupture of the microparticles. In other cases, control of the time delay for release of the agent is achieved by varying the polymer shell size and thickness of the microparticles. Producing microparticles of different sizes will result in their rupture and release of their core substance at different times. This will generate a constant rate of release of the encapsulated agent over a relatively long period of time. There are many methods which may be employed to allow for release of the agent at a constant rate over time. As readily apparent to one of skill in the relevant art, the duration of release and action of the rupture indicator in the body can be controlled by manipulation of several factors, alone or in combination, including but not limited to the following: polymer composition; rate of hydrolysis of the polymeric matrix; polymer:drug ratio; microparticle size; excipients; and concentration of residual solvent remaining in the microparticle.

The present invention may include controlling any of the foregoing but is not limited to: any particular method of synthesis of a microparticle and/or encapsulation of the biologically compatible rupture indicator therein; any particular size or type of microparticle; nor any particular means of sustained delivery of the encapsulated rupture indicator using microparticle technology which is currently known in the art and which may be further developed. "Microencapsulated rupture indicator" as referred to herein includes any and all methods of synthesis of the rupture indicator and microparticle technology that would achieve stabilization of, sustained released of, and/or prolonging of the signal or warning to the patient triggered by leaking out of the microencapsulated rupture indicator and degradation of the microparticle, slowly releasing the rupture indicator. "Microencapsulated rupture indicator" as referred to herein refers to any biologically compatible in that it is safe and appropriate for use in the human body and may be provided within a delivery system, such as a microparticle or like technology for sustained release. Further, "microencapsulated rupture indicator" may refer to one type of rupture indicator or a plurality of rupture indicators that are provided in either the same or different microparticles, or the like, and placed in the implant. Thus, "microencapsulated rupture indicator" may refer to one or more rupture indicators provided in stabilized and/or sustained release form. Thus, potentially, more than one signal or warning may resultantly be triggered upon leakage of the microencapsulated rupture indicator.

The state of the art with regard to materials and the processes for fabricating polymer-based sustained release devices such as microparticles and incorporating active therapeutic agents therein with subsequent selected release profiles, is described in detail in numerous patents, such as: U.S. Pat. No. 6,290,983, U.S. Pat. No. 5,817,343, U.S. Pat. No. 5,912,015, U.S. Pat. No. 5,989,463, U.S. Pat. No. 6,194,006, U.S. Pat. No. 6,379,703, U.S. Pat. No. 6,596,316, U.S. Pat. No. 6,455,074, U.S. Pat. No. 6,793,938, U.S. Pat. No. 6,296, 842, U.S. Pat. No. 6,479,065, U.S. Pat. No. 6,361,798 and U.S. Pat. No. 4,897,268. All of the preceding Patents are herein incorporated by reference in their entirety. In addition, the following Monograph is herein incorporated by reference in its entirety: Yao Liu, Nicolas Tsapis, and David Edwards, Division of Engineering and Applied Sciences (DEAS), Harvard University, MRSEC REU Program 2003, *Investigating Sustained-release Nanoparticles for Pulmonary Drug Delivery*.

In one aspect of the present invention, a biocompatible rupture indicator may be incorporated in the form of solid solutions or solid dispersions encapsulated within microparticles, or absorbed, incorporated into, or chemically bound to (or onto) an agent which is encapsulated within microparticles.

In another aspect of the present invention, a prosthesis comprises a microencapsulated biocompatible rupture indicator capable of sustained release.

In another aspect of the present invention, a method of constructing a prosthesis comprises encapsulating a biocompatible rupture indicator within microparticles and disposing the microparticles within the prosthesis to achieve sustained release of the rupture indicator and sustained delivery of the signal or warning to the patient, allowing for an increased time for the patient to detect the signal or warning.

In another aspect of the present invention, a prolonged signal or warning period is achieved by the extension of the shelf-life of the biologically compatible rupture indicator. The prosthesis comprises a biologically compatible ruptured indicator contained within microparticles or microcapsules. Upon compromise or rupture of the prosthesis, there is leaking out or release of the microparticles and subsequent sustained release of the rupture indicator contained therein into the tissues of the patient. The biologically compatible rupture indicator would then cause a bodily change and/or release a signal or warning in a sustained release manner as it is likewise slowly released from the microparticles.

In another aspect of the present invention, a prosthesis providing for an extension of the in vivo "shelf life" or "period of therapeutic effect" of the rupture indicator to provide the patient with a signal or warning for a prolonged period of time, giving her ample time to notice the signal. For instance, in the case of the patient noticing urine color change, as would be the case when the biologically compatible rupture indicator is selected to be phenazopyridine, a preferable period of time during which the urine would undergo color change, for purposes of the present invention and to ensure that the patient noticed the signal or warning, would be a period from about 5 to about 7 days.

The microencapsulated biologically compatible rupture indicator can trigger various signals or warnings to the patient. One type of rupture indicator may cause a color change to the patient's body excretion or secretion. Suitable examples include, but are not limited to, phenazopyridine hydrochloride, or biocompatible dyes such as aurintricarboxylic acid (ATA), halogenated ATA, sulfonated ATA, sulfonated-halogenated ATA, phosphorylated ATA, anazolene sodium, eosine I bluish, eosine yellowish, erythrosine, Evan's blue (EB), fast green FCF, fuchin(e) acid, iodophthalein sodium, rose bengal, sulfobromophthalein sodium, suramin sodium, trypan blue, trypan red, rosaniline chloride, crystal violet, methyl blue, methyl green, methylene blue, coomassie blue, basic fuchsin, malachite green, brilliant green, aniline blue, brilliant cresyl blue, safranin O, ethyl violet, pararosaniline acetate, methyl violet, direct yellow, direct red, ponceau S, ponceau SS, nitrosulfonazo III, chicago sky blue 6B, calcion or RG13577, and commonly used food dyes such as FD&C red No. 3, FD&C red No. 40, FD&C blue No. I and FD&C yellow No. 5.

As a result, a distinct color or smell, which is different from the normal color or smell of the excretion (e.g. urine or feces) or secretion (e.g. perspiration), would be noted by the patient as a warning of rupture or impending rupture and leaking of the implant filling material. Another type of rupture indicator indictor may trigger a change in taste of the saliva of the patient. As a result, the distinct taste, which is different from the normal taste of the saliva of the patient, would be noted by the patient as a warning of rupture or impending rupture and leaking of the implant filling material. Another type of rupture indicator indictor may trigger a sensation felt by the patient, locally about the place of implantation. The types of "bodily changes" experienced by the patient and noted by senses, i.e. sight, smell, touch, are provided as examples and are the invention is not limited thereto. Other self-detection means, such as a self-administered blood test, such as those used by diabetic patients who monitor their sugar levels, may be employed detecting the rupture indicator or a metabolized product thereof within the bloodstream of the patient.

In another aspect of the present invention, a prosthesis further comprises an indicator lumen, with the microencapsulated rupture indicator contained within the indicator lumen. Upon rupture of the exterior silicone elastomer envelope of the indicator lumen, there is leaking out or release of the microencapsulated rupture indicator into the tissues of the patient. The microencapsulated rupture indicator, as the microparticle or microsphere degrades and releases the rupture indicator, would then cause a bodily change and/or release a signal or warning in a sustained release manner.

In another aspect of the present invention, where microparticles are described as containing the biologically compatible rupture indicator, nanoparticles can be substituted wherever microparticles are used in the aforementioned description of the invention. Poly-lactic-glycolic acid (PLGA) nanoparticles have been investigated for sustained drug-release properties. The PLGA particles (approx. 200 nm) appear to incorporate the drug estradiol with 90% or greater efficiency.

The microencapsulated biologically compatible chemical indicators and the method of detection of implant rupture are specifically described herein in relation to breast prostheses. It should be understood, however, that the materials and methods can also be used for other cosmetic and reconstructive prostheses, such as brow, nose, cheek, chin, lips, pectoral, triceps, biceps, genitals, buttocks and calf.

Generally, the prosthesis comprises an external lumen enclosed by an external envelope made of at least one layer of an elastomer containing therein a biologically compatible chemical indicator for indicating rupture of the prosthesis and a carrier material, and an internal lumen enclosed by an internal envelope made of at least one layer of an elastomer containing therein an implant filling, material. The internal lumen is disposed within the external lumen. It is noted that the term "envelope" used herein may also commonly be referred to as a shell.

The rupture of a prosthesis is defined herein as the development of a tear or a hole in the envelope or shell of the prosthesis. A range of rupture characteristics that have been reported in the literature are included, from foci involving very small holes with a very small amount of silicone gel present outside of the envelope or shell, to larger visible physical tears and complete destruction with the prosthesis envelope or shell surrounded by silicone gel.

Figure 1:
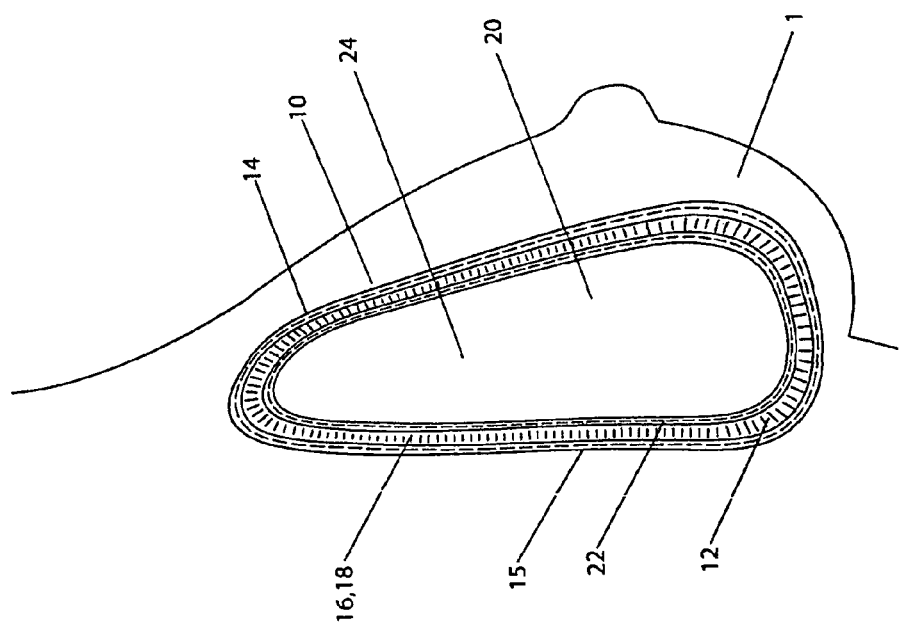
FIG. 1 is a side view of a double lumen breast prosthesis in one embodiment of the present invention which has an external envelope containing therein a biologically compatible chemical indicator in a carrier medium and an internal envelope filled with an implant filling material.

As shown in FIG. 1, a breast prosthesis 10 implanted in a human breast 1 includes an external lumen 12 enclosed by an external envelope 14. The external lumen 12 is filled with a microencapsulated biologically compatible chemical indicator 18 in a carrier medium 16 (shown by cross hatching). Preferably the carrier medium is a fluid material which has a low viscosity such as an aqueous solution. The breast prosthesis 10 also includes an internal lumen 20 enclosed by an internal envelope 22. The internal lumen 20 is filled with an implant filling material 24, preferably a material having a much higher viscosity such as a silicone gel.

Suitable examples of implant filling materials include, but are not limited to, glycosaminoglycan including hyaluronic acid, chondroitin 4-sulfate, chondroitin 6-sulfate, dermatan sulfate, heparin sulfate, and keratin sulphate; mucopolysaccharide, polyvinylpyrollidone, polyvinyl pyrralidone, polyvinyl alcohol, polyacrlimides, polysaccharides, hydroxypropylmethyl cellulose, polyethylene oxide, hyaluronic acid, sodium or calcium alginate, hydrogel polyurethane, hydroxyethyl starch, polyglycolic acid, polyacrylamide, hydroxyethylmethacrylate (HEMA), and naturally derived biopolymers including sodium kinate, seaweed, and agar; aqueous solution of polyethylene glycol; linear or branched, or crosslinked polyacrylamide, sodium hyaluronate, phosphatidylcholine (PC), hydroxypropylmethyl cellulose (HPMC) and its derivatives including hydroxyalkyl cellulose, sodium carboxymethyl cellulose, hydroxyethyl cellulose, hydroxypropyl cellulose, methylhydroxypropyl cellulose, methyl cellulose and ethylhydroxyethyl cellulose; arid polyoxyethylene polyoxypropylene block copolymers which have gelling properties at body temperature. Furthermore, the implant filling material can also be a saline solution.

Suitable examples of the carrier medium include, but are not limited to, aqueous solution, physiological saline solution, oil, water soluble gel, and other biocompatible fluid materials. Preferably, the carrier medium is isotonic.

The external envelope 14 and internal envelope 22 are made of at least one layer of a soft flexible biocompatible material such as a silicone elastomer. Suitable materials include, but are not limited to, silicone elastomers such as, polydimethylsiloxane, polymethylvinylsiloxane, copolymers thereof, or heterpolymers of diphenylpolysiloxane and dimethylpolysiloxane having diphenyl polysiloxane substituents. Other polymers may be substituted as will be apparent to those skilled in the art. The external envelope 14 and internal envelope 22 can be made of the same material or different materials.

In one embodiment, the internal envelope 22, or external envelope 14, or both, can be constructed of two or three layers of silicone elastomer to reduce silicone diffusion and enhance the strength of the envelope. One suitable example has been described in U.S. Pat. No. 4,455,691, which is herein incorporated by reference. More specifically, the envelope can be made of three layers, with inner and outer layers made of the silicone elastomer described above, and a middle layer in-between functioning as a barrier to silicone diffusion. The middle layer can be made of a reaction product of dimethylpolysiloxane and siloxane elastomer such as 3,3,3-trifluoropropylpolysiloxane, diphenylpolysiloxane, or methylphenylpolysiloxane. It is noted that the elastomer of the inner/outer layers of the internal envelope may be the same as the material used for the external envelope, or alternatively they may be different from the material.

Furthermore, the commercially available material, known as low diffusion silicone elastomer shell produced by the INAMED Corporation (Santa Barbara, Calif.), can be used for construction of the internal and external envelopes for the purpose of the present invention. The low diffusion silicone elastomer shell is made of two layers of silicone elastomer with a barrier coat between the two layers. The barrier coat can be the reaction product of dimethyl-polysiloxane and siloxane elastomer as described above.

In another embodiment, the external envelope 14 can have a multi-layer structure comprising a hydrophobic thermoplastic elastomer layer which functions as a water vapour barrier for maintaining the aqueous filling material at the desired osmotic balance in the envelope. This effect can reduce implant rupture through fold flaw fracture caused by loss of water vapour. The materials and the process of making the multi-layer envelope has been described in detail in U.S. Pat. No. 5,630,844, which is herein incorporated by reference in its entirety. More specifically, the inner and outer layers can be made of silicone elastomer, and the middle layer is made of a thermoplastic elastomer such as styrene block copolymers, or a mixture of styrene block copolymers and ethylene-propylene based copolymers which are thermoplastic elastomers. Preferably, the thermoplastic elastomers have tri-block copolymers with styrene end-blocks and a mid-block of an elastomer polymer selected from olefin, vinyl, and dienyl based polymers.

As illustrated, the external envelope 14 has a generally tear-drop shape with a relatively flat rear portion 15 and rounded dome or a forward surface 17. The external envelope 14 defines an external lumen which may be of a generally teardrop shape or other non-symmetrical shape in order to conform to the contours of a human breast. It should be recognized that in certain cases a round shape may be desirable.

Although the prosthesis and the method of use of the present invention have been described above with a double lumen breast implant structure, it should be understood that other implant structures can also be used with the biologically compatible microencapsulated rupture indicators described above. In general, the prosthesis comprises an indicator lumen enclosed by an indicator lumen envelope made of at least one layer of an elastomer containing therein a biologically compatible chemical indicator for indicating rupture of the prosthesis and a carrier medium; and at least one implant lumen enclosed by an implant lumen envelope made of at least one layer of an elastomer, disposed within the indicator lumen, wherein the implant lumen containing therein an implant filling material. Herein, for the purpose of description of the instant invention, the term "implant lumen" denotes a lumen being filled with an implant filling material, such as a silicone gel, or a saline solution, without a rupture indicator. Preferably, the indicator lumen is disposed at the most exterior of the prosthesis.

It is apparent that the prosthesis structure illustrated in FIG. 1 is one specific example, with one implant lumen disposed with the indicator lumen. As another example shown in FIG. 2, the prosthesis 50 comprises an internal implant lumen 52 disposed within an external implant lumen 54, and an indicator lumen 56 disposed outside the external implant lumen, with each lumen enclosed by its envelope. In this case, the prosthesis has a triple lumen structure, with the most exterior lumen as the indicator lumen. The internal and external implant lumens can be filled with a same or different implant filling materials, wherein these two lumens can be structured either in the form of the traditional double lumen or in the form of the reversed double lumen breast prosthesis known in the breast implant industry.

Since the indicator lumen is located at the most exterior of the prosthesis, when the prosthesis ruptures, the microencapsulated rupture indicator releases into the tissues where it is absorbed and subsequently indicates the rupture in one of the mechanisms described above.

Figure 3:
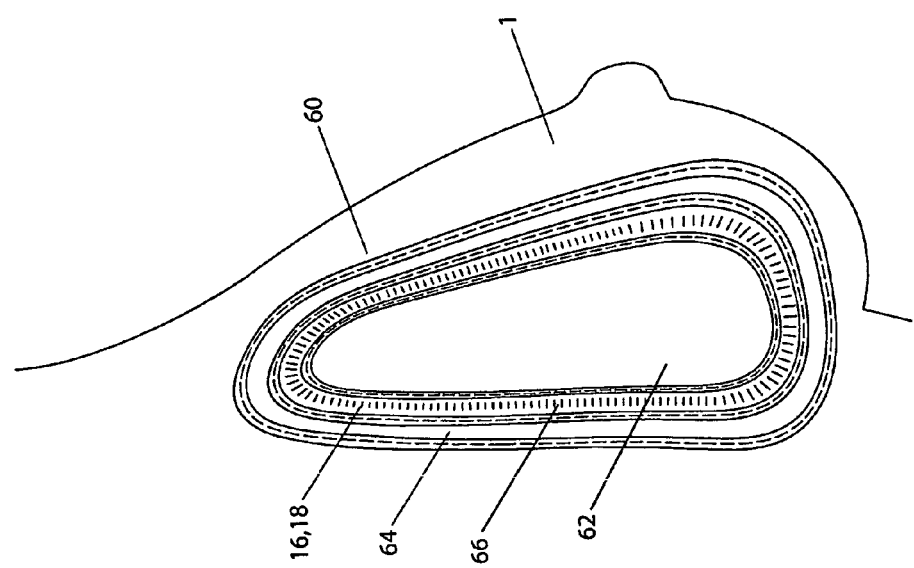
FIG. 3 is a side view of a triple lumen breast prosthesis in another embodiment of the present invention, which has the indicator lumen disposed outside the internal implant lumen and within the external implant lumen.

In an alternative embodiment as shown in FIG. 3, the breast prosthesis 60 has the indicator lumen 66 disposed outside the internal implant lumen 62 and within the external implant lumen 64. This structural arrangement is suitable for the traditional double lumen breast implant, wherein the internal implant lumen 62 is filled with a silicone gel, and the external implant lumen 64 is filled with a saline solution. In this situation, when the chemical indicator releases into the body, it indicates the rupture or damage of the external implant lumen, and a potential damage of the internal implant lumen envelope.

Figure 4:
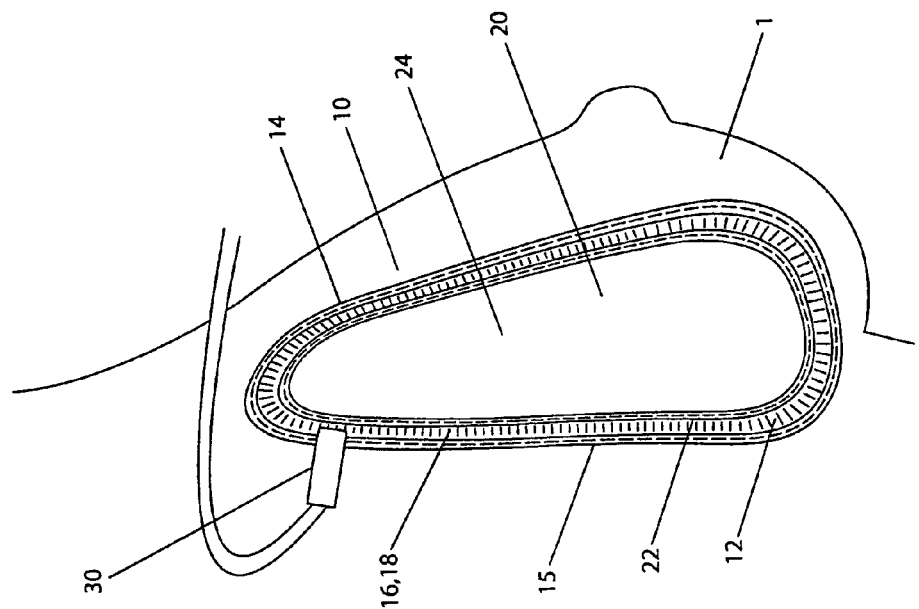
FIG. 4 is a side view of the double lumen breast prosthesis shown in FIG. 1, which further includes a filling tube.

A further embodiment of the present invention includes means for adding or 20 removing the microencapsulated rupture indicator 18 in the carrier medium 16 to or from the external lumen 12 and/or the implant filling material 24 to or from internal lumen 20. One such means is illustrated in FIG. 4. As shown, a filling tube 30 is in an inserted position within the external lumen 12 and can be inserted at the time of manufacture. Alternatively, a filling tube can be inserted later. The filling tube 30 is typically inserted through a self-sealing valve (not shown) commonly used in breast implant surgery. The distal end of filling tube 30 is connected with a source of the chemical indicator or implant filling material. Upon completion of the filling process, the filling tube 30 is removed and the self-sealing valve closes. Furthermore, other filling valves currently used in the breast implant industry, such as the filler valve on the Becker Expandable breast prosthesis by Mentor Corporation, Santa Clara, Calif., can also be incorporated into the prosthesis structure of the present invention.

Using the breast prosthesis containing a microencapsulated rupture indicator and the method of detection, the potential rupture of the breast prosthesis can be conveniently detected. With the present invention, an early detection of the rupture is possible. Since when microencapsulated rupture indicator contained in the external lumen 12 leaks out, it indicates a potential problem of the breast prosthesis, even if the internal envelope has not ruptured. A further confirmation examination can be performed using MRI. The present invention signals the patient directly to seek such medical attention and prevent any mal-effects of leakage of implant filling material out of the prosthesis.

Figure 5:
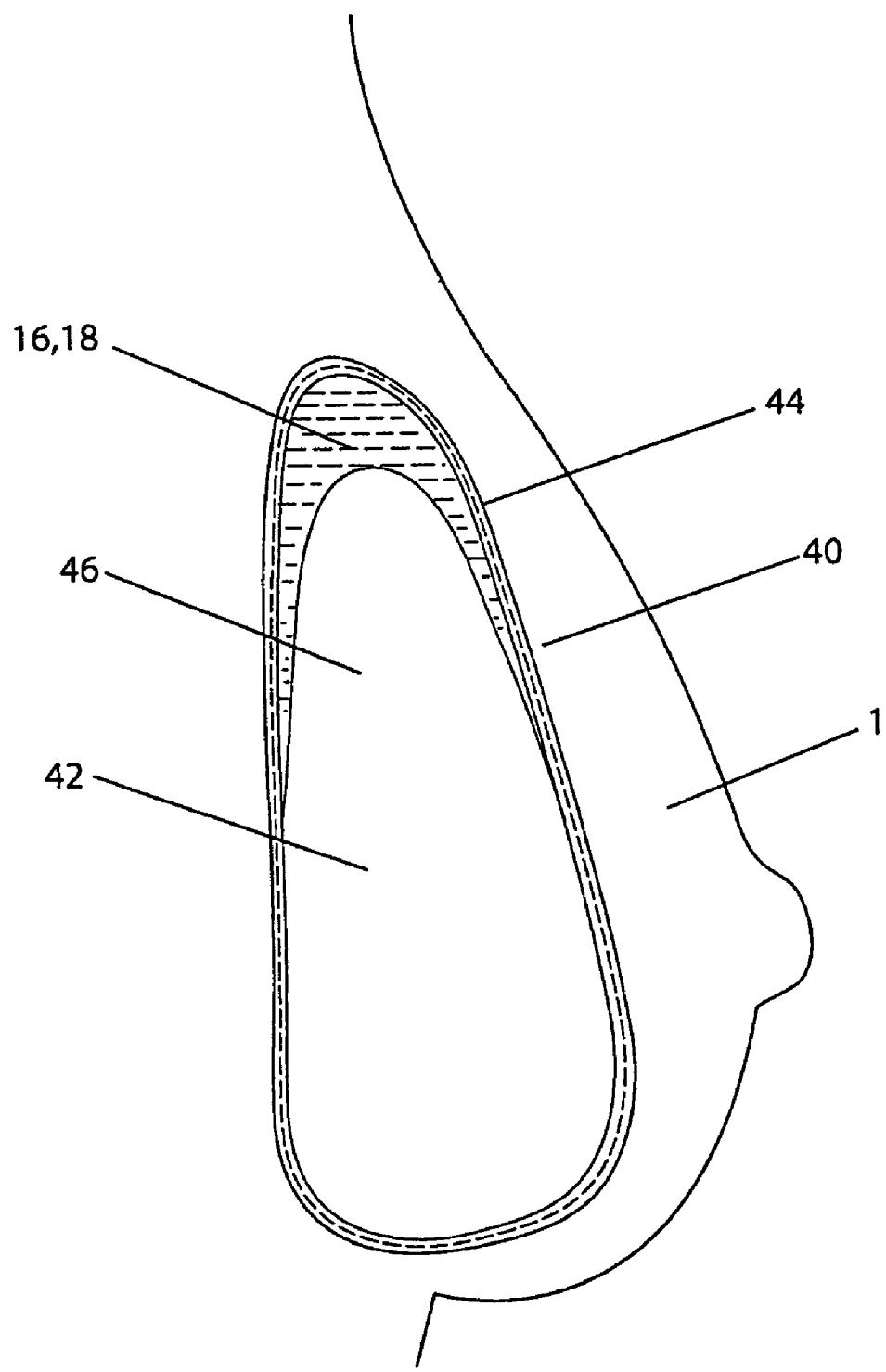
FIG. 5 is a side view of a single lumen breast prosthesis in a further embodiment of the present invention, which is enclosed by an envelope containing therein an implant filling material and a chemical indicator in a carrier solution.

In another embodiment, the present invention provides a single lumen prosthesis containing a microencapsulated rupture indicator. As shown in FIG. 5, a breast prosthesis 40 implanted in a human breast 1 includes single lumen 42 enclosed by an envelope 44. The single lumen 42 is filled with an implant filling material 46, such as silicone gel or other suitable filling materials as described above, and a microencapsulated rupture indicator 18 in a carrier medium 48. Suitable microencapsulated rupture indicators have been described above. Preferably, a water soluble microencapsulated rupture indicator is used with an aqueous solution as the carrier medium so that when the breast prosthesis ruptures the microencapsulated rupture indicator releases out into the tissues and then is absorbed into the vascular system. It is noted that the relative position of the implant filling material 46 with respect to the position of the carrier medium 48 can vary depending on the densities of the filing material and the carrier medium, as well as the position of the body. In other words, the implant filling material can be either above or below the carrier medium containing the microencapsulated rupture indicator.

The carrier medium 48 can be an aqueous solution such as a saline solution, and can further contain an antimicrobial as preservative. Moreover, the carrier medium can further contain a surfactant. The surfactant in the carrier medium forms micelles which attract and maintain the organic indicator molecules in the carrier medium.

In an exemplary embodiment, single lumen 42 contains 85% or more in volume of the filling material 46 and 15% or less in volume of the chemical indicator in the carrier medium.

A double lumen breast implant having a structure shown in FIG. 1 has a silicone gel commonly used in the breast implant as the filling material inside the internal lumen 20. The external lumen contains from about 35 to about 45 ml of sterilized aqueous solution of methylene blue. The methylene blue is in a concentration range from about 1 mg/ml to about 4 mg/ml. With the concentration and volume of the methylene blue described, it is in a range from about 1 to about 2 mg per kilogram of body weight for an average female (from about 50 to about 70 kg). In the event of rupture, the methylene blue solution leaks out from the external is lumen into the tissues where it is absorbed into the vascular system, metabolizes in kidney, and releases to urine, which causes a color change of the urine.

Furthermore, the dye used for the purpose of the present invention is preferably water soluble so that it can release out through body excretion or secretion, such as urine, saliva, perspiration, and feces, or in peripheral blood when the prosthesis ruptures. When the prosthesis ruptures, even a minor rupture, the microencapsulated rupture indicator 18 leaks out from external lumen 12 into the tissues where it is absorbed into the vascular system of the body. Optionally, microencapsulated rupture indicator 18 can also be contained in the internal lumen 20, which will leak out when both envelopes rupture. In one embodiment, the leaked microencapsulated rupture indicator 18 can be visually detected in urine, or saliva. It can also be detected in a body excretion or secretion sample or a peripheral blood sample using a colorimetric method. Such detection can be performed in a clinical laboratory, or can be performed using a specifically designed kit for home use, similar to the glucose, or pregnancy test kits.

The Example described hereinafter provides a detailed configuration of the breast implant of the present invention and the method of detection. In an exemplary embodiment of a breast implant, the filling material in the internal lumen is 85% or more of the total volume of the prosthesis for maintaining the overall prosthesis properties, and the fluid material in the external lumen is 15% or less. The ratio between the filling material and the fluid material in the external lumen can be different for different types of prostheses.

With water soluble dyes, the rupture can also be visually detected by staining of skin locally (i.e. skin near the implantation site of the of the prosthesis) by the leaked dye. Furthermore, in addition to dyes, other non-coloring biocompatible microencapsulated rupture indicator, detectable at a trace amount, can also be used, which can be detected in body excretion, such as urine or feces, or secretion, such as saliva and perspiration, or in peripheral blood (i.e., blood circulating through the patient's blood stream), using a chemical reaction which is sensitive and specific to the indicator.

Another type of microencapsulated rupture indicator is an odour generating material which causes a smell change of body excretion or secretion, such as saliva, urine, perspiration and feces, or a taste change in the saliva. One example is a sterilized garlic solution. When the breast prosthesis ruptures, the odour generating solution leaks into the tissues where it is absorbed into the vascular system, and subsequently causes an unusual body odor in a sustained release fashion, hence, alert the user.

This invention is applicable to all implants used in cosmetic and reconstructive surgery using silicone gel as the implant filling material, such as brow, nose, cheek, chin, lips, pectoral, breast, triceps and biceps, genitals, buttocks and calf. Among these, some require a small amount of implant filling material, some require a large amount of filling material. For example, the calf implant is inserted to rebalance legs affected by such diseases as polio, which requires a relatively large amount of filling material. In general, the larger the amount of implant filling material, the worse the potential impact of filling material to a patient can be. Therefore, the benefits of the present invention as a cost effective and more convenient method for a patient's self-detection of the rupture applies to all silicone gel-filled cosmetic and reconstructive implants.

Most importantly, all of the aforementioned occurs before there is any leakage of silicone-gel into the breast tissues in a prosthesis in which the microencapsulated biologically compatible rupture indicator is contained in an indicator lumen, separate from the silicone-gel or an alternative filling material. Alternatively, in a single lumen implant in which the microencapsulated biologically compatible indicator is contained in the same lumen as the filling material, the biologically compatible indicator, through sustained release, would provide an early signal or warning to the patient that the specific filling material has been exposed to the breast tissues and immediate medical attention is warranted.

The above description is for the purposes of teaching the person of ordinary skill in the art how to practice the present invention, and it is not intended to detail all those obvious modifications and variations of it which will become apparent to the skilled worker upon reading the description.

What is claimed is:

1. A prosthesis for implant in a human patient body, comprising:
   an external envelope made of at least one layer of a first elastomer;
   at least one indicator lumen enclosed by the external envelope;
   a carrier medium disposed within the indicator lumen;
   at least one biologically compatible microencapsulated rupture indicator contained in the carrier medium, the rupture indicator capable of leaking out of the indicator lumen upon rupture of the external envelope and triggering a signal detectable by the patient;
   at least one implant lumen enclosed by at least one implant lumen envelope made of at least one layer of a second elastomer, the implant lumen disposed within the indicator lumen; and an implant filling material contained within the implant lumen; and
   wherein the signal is a distinct color in urine of the patient detectable by sight; and
   wherein the microencapsulated rupture indicator is phenazopyridine.

2. The prosthesis of claim 1, wherein the implant filling material is selected from the group consisting of silicone gel and saline solution.

3. The prosthesis of claim 1, wherein the microencapsulated rupture indicator comprises a rupture indicator encapsulated in a sustained release delivery system prior to placement in the carrier medium, the sustained release delivery system selected from the group consisting of a microparticle, microsphere, nanoparticle, nanosphere, and combinations of these.

4. The prosthesis of claim 3, wherein selection of the particular sustained release delivery system controls the rate of sustained release of the rupture indicator triggering the signal to the patient.

5. The prosthesis containing a rupture indicator of claim 1, further comprising an external implant lumen which is enclosed by an external implant lumen envelope, and an internal implant lumen enclosed by an internal implant lumen envelope, the internal implant lumen disposed within the external implant lumen envelope.

6. The prosthesis of claim 5, wherein the external implant lumen is disposed internally within the indicator lumen such that the carrier medium surrounds the implant lumen and the implant filing material contained therein.

7. The prosthesis of claim 5, wherein the implant filling material contained in the internal implant lumen is a silicone gel.

8. The prosthesis of claim 5, wherein the implant filling material contained in the external implant lumen is a saline solution.

9. The prosthesis of claim 1, wherein the indicator lumen comprises a filling means for filling the microencapsulated rupture indicator and the carrier medium through the exterior envelope.

10. The prosthesis of claim 1, wherein the exterior envelopes comprise a first inner layer and a first outer layer, both made of the first is elastomer, and a first barrier layer between the first inner and the first outer layers.

11. The prosthesis of claim 1, wherein the indicator lumen envelope comprises a first inner layer and a first outer layer, both made of the first elastomer, and a first barrier layer between the first inner and first outer layers.

12. The prosthesis of claim 1, wherein the implant lumen envelope comprises a second inner layer and a second outer layer, both made of the second elastomer, and a second barrier layer between the second inner and second outer layers.

13. A prosthesis for implant in a human patient body, comprising:
- an external envelope made of at least one layer of a first elastomer;
- at least one implant filling material contained within the external envelope; and
- at least one biologically compatible rupture indicator encapsulated in a sustained release delivery vehicle and disposed in a carrier medium for placement in the external envelope, the rupture indicator capable of leaking out of upon rupture of the external envelope and triggering a signal detectable by the patient as it is released from the delivery vehicle; and wherein the microencapsulated rupture indicator is phenazopyridine.

14. The prosthesis of claim 13, wherein the sustained release delivery vehicle is selected from the group consisting of a microparticle, microsphere, nanoparticle, nanosphere, and combinations of these.

15. The prosthesis of claim 14, wherein selection of the particular sustained release delivery system controls the rate of sustained release of the rupture indicator triggering the signal to the patient.

* * * * *